US006998129B2

(12) United States Patent
Breton et al.

(10) Patent No.: US 6,998,129 B2
(45) Date of Patent: *Feb. 14, 2006

(54) COSMETIC OR DERMATOLOGICAL COMPOSITION COMPRISING AN ASSOCIATION BETWEEN AN ELASTASE INHIBITOR COMPOUND OF THE N-ACYLAMINOAMIDE FAMILY AND AT LEAST ONE ANTI-INFLAMMATORY COMPOUND

(75) Inventors: Lionel Breton, Versailles (FR); Yann Mahe, Morasng sur Orge (FR)

(73) Assignee: L'Oreal, Paris (FR)

( * ) Notice: Subject to any disclaimer, the term of this patent is extended or adjusted under 35 U.S.C. 154(b) by 143 days.

This patent is subject to a terminal disclaimer.

(21) Appl. No.: 10/179,955

(22) Filed: Jun. 26, 2002

(65) Prior Publication Data

US 2003/0072732 A1 Apr. 17, 2003

(30) Foreign Application Priority Data

Jun. 26, 2001 (FR) .................................. 01 08434

(51) Int. Cl.
 *A61K 6/00* (2006.01)
 *A61K 7/00* (2006.01)
 *A61K 38/00* (2006.01)

(52) U.S. Cl. .......................................... 424/401; 514/2

(58) Field of Classification Search ................ 424/401; 514/2
See application file for complete search history.

(56) References Cited

U.S. PATENT DOCUMENTS

2003/0072732 A1 4/2003 Breton et al.

FOREIGN PATENT DOCUMENTS

| EP | 0 764 444 | | 3/1997 |
| EP | 0 974 586 | | 1/2000 |
| EP | 1 002 536 | | 5/2000 |
| FR | 2 810 033 | | 12/2001 |
| JP | 2000-178163 | * | 6/2000 |
| WO | WO 00/12467 | | 3/2000 |

OTHER PUBLICATIONS

Patent Abstracts of Japan; vol. 2000, No. 23, Feb. 10, 2001; & JP 2001 158732; Jun. 12, 2001.
Nakamura, M. et al.; "A Two-Step, One-Pot Synthesis of Diverse N-Pyrucoyl Amino Acid Derivatives Using the Ugi Reaction"; Bioorganic & Medicinal Chemistry Letters; Oxford, GB; vol. 10, No. 24, Dec. 18, 2000, pp. 2607-2810, XP004225356.
Database WPI, Section Ch, Week 200026, Derwent Publications Ltd., London, GB; Class D21, An 2000-298811 XP002196277 & JP 2000 087081; (Lion Corp); Mar. 28, 2000.
U.S. Appl. No. 11/065,356, filed Feb. 25, 2005.

* cited by examiner

*Primary Examiner*—Shengjun Wang
(74) *Attorney, Agent, or Firm*—Oblon, Spivak, McClelland, Maier & Neustadt, P.C.

(57) ABSTRACT

A cosmetic or dermatological composition characterized in that it comprises an association between an elastase inhibitor compound of the N-acylaminoamide family and at least one anti-inflammatory compound.

14 Claims, No Drawings

COSMETIC OR DERMATOLOGICAL COMPOSITION COMPRISING AN ASSOCIATION BETWEEN AN ELASTASE INHIBITOR COMPOUND OF THE N-ACYLAMINOAMIDE FAMILY AND AT LEAST ONE ANTI-INFLAMMATORY COMPOUND This application claims foreign priority of France 01 08434, filed Jun. 26, 2001.

The present invention relates to the field of cosmetic or dermatological compositions. It relates to novel cosmetic or dermatological compositions comprising an association between an elastase inhibitor compound of the N-acylaminoamide family and at least one anti-inflammatory compound. Such a composition is preferably adapted for improving the skin ageing and/or photoageing signs by slowing down the connective tissue alterations and by improving the skin functional condition, and, more particularly, the signs associated with or resulting from an inflammatory process, in particular a chronic micro-inflammatory process.

The human skin consists in two compartments, i,e. a superficial compartment, the epidermis, and a deep compartment, the derma. The natural human epidermis mainly comprises three cell types, which are the keratinocytes, much in the majority, the melanocytes and the Langerhans cells. Each of such cell types contributes, by virtue of its own functions, to the essential part played in the skin organism.

The derma provides a solid support to the epidermis. It is also its nutritive element. It consists mainly in fibroblasts and one extracellular matrix, comprising, in its turn, mainly collagen, elastin and one substance, the so-called fundamental substance, formed with components synthetized by the fibroblast. It also comprises leukocytes, mastocytes or even tissue macrophages. It is also crossed by blood vessels and nervous fibres.

It is known that during a superficial skin stress, which can normally be from chemical, physical or bacterial origin, the keratinocytes from the epidermis superficial layers release biological mediators which are adapted to attract some of the skin infiltrating cells, which are themselves responsible for maintaining a transitory local irritation.

Biological mediators able to be produced by the thus-stressed keratinocytes include chemokines which are chemoattractive cytokines responsible for recruiting leukocytes on inflammatory sites, including the interleukin 8 (IL-8) which is more particularly responsible for recruiting neutrophils, Such cells infiltrating into the irritated or attacked areas then release enzymes, amongst which the leukocyte elastase can be found. Under the action of such enzyme among others, the extracellular backing elastic fibres in connective tissue may be altered and thereby lead to a reduction of skin elasticity.

Further, it is also known that in synergy with cathepsin G, the leukocyte elastase may dissociate the epidermis integrity by enlarging the Interkeratinocyte intercellular spaces.

Thus, in the long term, the sum of the superficial skin micro-stresses generated, for example, by a prolonged UV exposure or by irritating agents, can lead to a more or less accelerated loss of skin natural elasticity. The array formed by the elastic fibres in the underlying connective tissue and the extracellular spaces can then be progressively dismantled. This results in an accelerated ageing of the skin (wrinkled and/or less supple skin) with the derma elastic array being altered, as well as more accentuated wrinkles (deeper wrinkles).

Upon a (chemical, physical, bacterial or neurogeneous) skin stress, the keratinocytes release biological mediators (called chemoattractive factors) which are able to attract some inflammatory cells of the blood compartment towards the skin tissue. Such cells are responsible for generating, and subsequently, for maintaining a local irritation.

Amongst the chemoattractive factors able to be produced by the stressed keratinocytes, the interleukin 8 (IL-8) is more specifically responsible for recruiting the neutrophil polynuclears. Such cells infiltrating into the irritated or attacked areas then release enzymes, including the leukocyte elastase.

Under the action of such enzyme, the extracellular backing elastic fibres in the connective tissue are altered. In synergy with the cathepsin G, the leukocyte elastase can also dissociate the epidermis integrity enlarging the Interkeratinocyte intercellular spaces (Ludolph-Hauser et al. Exp. Dermatol. 1999 8(1) 46–52). The leukocyte elastase has recently been incriminated in maintaining eschars and in producing leg venous ulcers, through its fibronectin altering activity (Herrick S et al. Lab. Invest. 1997(3) 281–288). The sum of the localized alteration micro-stresses (resulting, for example, from a prolonged exposure to the sun) can result in the long term in an accelerated loss of the natural elasticity in skin. The underlying connective tissue elastic fibre and the extracellular space array is then progressively dismantled. This accelerated alteration can be cumulated with the skin normal ageing process which Is characterized by a higher sensitivity of the elastic fibres to the elastase action (Stadler R & Orfanos CE Arch. Dermatol. Res. 1978 262(1) 97–111).

It is known in the state of the art that molecules can be brought in the skin tissue so as to slow down the alteration activity of the elastic fibres In the intercellular spaces.

The technical solution according to the invention is to bring, in addition to the regulating element downstream of the elastase activity (i.e. the N-acylaminoamide derivative inhibiting the enzymatic activity of the leukocyte elastase, the {2-[acetyl-(3-trifluoromethyl-phenyl)-amino]-3-methylbutyrylamino}acetic acid, one or more active Ingredients adapted to also regulate the early Inflammatory events further upstream. According to one embodiment, the product to be associated in the formula prevents the production cascade for the proinflammatory cytokines such as IL-8, TNF or IL-1.

Consequently, the object of the invention is to provide a cosmetic or dermatological composition characterized in that it comprises an association between an elastase inhibiting compound of the N-acylaminoamide family and at least one anti-inflammatory compound.

Another object of the invention is a cosmetic treating method for the body or the face skin, Including the scalp, wherein a cosmetic composition such as defined above is applied onto the skin.

It has been found indeed that the N-acylaminoamide compounds, and, more particularly, the compounds of the formula (I) show an inhibiting activity for the elastase activity and that they can consequently be used for limiting and/or fighting the elastic fibre alteration.

Therefore, they can be used in or for preparing a composition, the compounds or the composition being designed to treat, in a preventive and/or curative way, the ageing skin signs.

The novel association of the N-acylaminoamides with at least one anti-inflammatory compound makes it possible to significantly reinforce the anti-ageing effect of the matrix tissue by bringing an anti-inflammatory effect.

The resulting composition is designed to treat ageing disorders and/or to be more specifically designed to treat all the skin disorders associated with an inflammation, in particular with a chronic micro-inflammatory process.

Preferably, this novel association is used in care and/or hygiene cosmetic preparations of the areas exposed to the sun (scalp, body, face, lips), in care and/or hygiene cosmetic preparations of the ulcerated areas, in tooth-pastes or mouth-wash lotions and, generally, in all the so-called "skin anti-ageing" cosmetic preparations with the objective of slowing down the chronobiological dismantling of the backing tissues and of the architecture of he skin matrix elements. More particularly, such association will be reserved for comedogenic and acne-suffering skins.

This novel association is also used in care cosmetic preparations for the areas exposed to the sun (scalp, body, face, lips), in care cosmetic preparations of the ulcerated areas, in tooth-pastes or mouthwash lotions and, generally, in all the so-called "skin anti-ageing" cosmetic preparations with the objective of slowing down the chronobiological dismantling of the support tissues and of the architecture of the skin matrix elements.

Without being bound by any theory, the Applicant thinks that bringing at the level of the skin superficial layer keratinocytes, compounds adapted to slow down the altering activity of the intercellular space elastic fibres, makes it possible to reduce this skin accelerated ageing phenomenon resulting from superficial cutaneous stresses and that the association of such compounds with an anti-inflammatory compound considerably reinforces their effects.

Preferably Preferred N-acylaminoamide Compounds

The compounds likely to be preferably used in the present invention have therefore the following formula (I):

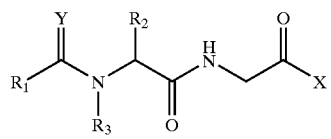

(I)

where:
the Y radical represents O or S,
the $R^1$ radical represents:
(i) a hydrogen atom,
(ii) a linear, branched or cyclic, saturated or unsaturated hydrocarbon radical having 1 to 18 carbon atoms, optionally substituted by 1 to 5 groups, either identical or different, selected amongst —OH; —OR; —O—COR; —SH; —SR; —S—COR; —NH$_2$; —NHR; —NRR'; —NH—COR; Hal (halogen); —CN; —COOR; —COR; —P(O)—(OR)$_2$; —SO$_2$—OR; with R and R' representing, independently from each other, a linear, branched or cyclic, saturated or unsaturated hydrocarbon radical having 1 to 6 carbon atoms, optionally being halogenated or even perhalogenated; said R and R' radicals being able to form together with N a carbon ring with 5 to 6 ring members optionally comprising further at least one heteroatom being selected amongst O, N and/or S In the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical, having 1 to 6 carbon atoms, optionally being halogenated, even perhalogenated;

(iii) a radical selected amongst —OR; —NH$_2$; —NHR; —NRR'; —NH—COR; —COOR; —COR;
with R and R' representing, independently from each other, a linear, branched or cyclic, saturated or unsaturated hydrocarbon radical having 1 to 6 carbon atoms, optionally being halogenated, even perhalogenated;
said R and R' radicals being able to form together with N a carbon ring with 5 to 6 ring members optionally comprising, additionally, at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated, even perhalogenated;

the $R^2$ radical represents a linear, branched or cyclic, saturated or unsaturated hydrocarbon radical, with 1 to 18 carbon atoms, optionally substituted by 1 to 5 groups, either identical or different, selected amongst —OH; —OR; —O—COR; —SH; —SR; —S—COR; —NH$_2$; —NHR; —NRR'; —NH—COR; Hal (halogen); —CN; —COOR; —COR; with R and R' representing, Independently from each other, a linear, branched or cyclic, saturated or unsaturated hydrocarbon radical, with 1 to 6 carbon atoms, optionally halogenated, or even perhalogenated; said R and R' radicals able to form together with N a carbon cycle with 5 to 6 chains optionally comprising, additionally, at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical, with 1 to 6 carbon atoms, optionally halogenated, even perhalogenated;

the $R^3$ radical represents a radical selected amongst those of the formulae (II) or (III)

(II)

(III)

where:
y is an integer between 0 and 5 inclusive, and y' is an integer between 1 and 5 inclusive;
A is a linear or branched, saturated or unsaturated hydrocarbon divalent radical, with 1 to 18 carbon atoms, optionally being substituted by 1 to 5 groups, either identical or different, selected amongst —OH; —OR; —O—COR; —SH; —SR; —S—COR; —NH$_2$; —NHR; —NRR'; —NH—COR; Hal (halogen or even perhalogen); —CN; —COOR; —COR; —NO$_2$; —SO$_2$OR;
with R and R' representing, independently from each other, a linear, branched or cyclic, saturated or unsaturated hydrocarbon radical, with 1 to 6 carbon atoms, optionally being halogenated or even perhalogenated;

said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated, even perhalogenated;

B is a linear or branched, saturated or unsaturated hydrocarbon radical having 1 to 18 carbon atoms, optionally substituted by 1 to 5 groups, either identical or different, selected amongst —OH; —OR; —O—COR; —SH; —SR; —S—COR; —NH$_2$; —NHR; —NRR'; —NH—COR; Hal (halogen or even perhalogen); —CN; —COOR; —COR; —NO$_2$; —SO$_2$OR; with R and R' representing, independently from each other, a linear, branched or cyclic, saturated or unsaturated hydrocarbon radical having 1 to 6 carbon atoms, optionally being halogenated or even perhalogenated; said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon having 1 to 6 carbon atoms, optionally being halogenated or even perhalogenated;

the X radical is a radical selected amongst —OH; —OR$_4$; —NH$_2$; —NHR$_4$; NR$_4$R$_5$; —SR$_4$; —COOR$_4$; —COR$_4$; with R$_4$ and R$_5$ representing, independently from each other, a linear, cyclic or branched saturated or unsaturated hydrocarbon radical having 1 to 6 carbon atoms, optionally substituted by 1 to 5 groups, identical or different, selected amongst —OH; —OR; —O—COR; —SH; —SR; —S—COR; —NH$_2$; —NHR; —NH—COR; -Hal (halogen, even perhalogen); —CN; —COOR; —COR; with R and R' representing, independently from each other, a linear, branched or cyclic, saturated or unsaturated hydrocarbon radical having 1 to 6 carbon atoms, optionally being halogenated or even perhalogenated; said R and R' radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; NH$_2$; —NHR"; —NH—COR"; -Hal (halogen); —CN; —COOR"; —COR", with R" representing a linear, branched or cyclic, saturated or unsaturated hydrocarbon radical having 1 to 6 carbon atoms, optionally being halogenated or even perhalogenated; said R$_4$ and R$_6$ radicals being able to form together with N a carbon ring with 5 to 6 ring members optionally comprising further at least one heteroatom selected amongst O, N and/or S in the ring and/or optionally substituted by 1 to 5 groups, identical or different, selected amongst —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon radical having 1 to 6 carbon atoms, optionally being halogenated or even perhalogenated.

Are also included In such definition, the mineral or organic acid salts of said compounds, as well as the optical isomers thereof, in an isolated form or as a racemic mixture.

It is meant by a linear, cyclic or branched hydrocarbon radical, amongst others radicals of the alkyl, aryl, aralkyl, alkylaryl, alkenyl or alkynyl type.

The $C_6H_5$ group present in the $R_3$ radical should be understood as an aromatic cyclic group.

Preferably, the Y radical represents oxygen,

Preferably, the $R_1$ radical represents hydrogen or a linear or branched, saturated or unsaturated hydrocarbon radical having 1 to 12, more particularly 1, 2, 3, 4, 5 or 6 carbon atoms, optionally being substituted. Amongst others, the substituants can be selected amongst —OH; —OR; and/or —P(O)—(OR)$_2$ with R representing a linear, branched or cyclic, saturated or unsaturated hydrocarbon radical having 1 to 6 carbon atoms, optionally being halogenated, even perhalogenated.

Preferably, the $R_1$ radical represents a methyl, ethyl, propyl or isopropyl radical optionally substituted by a —OH or —P(O)—(OR)$_2$ group with R representing methyl, ethyl, propyl or isopropyl.

Preferably, the $R_2$ radical represents a linear, branched or cyclic, saturated or unsaturated hydrocarbon radical having 1 to 12, more particularly, 1, 2, 3, 4, 5 or 6 carbon atoms, optionally substituted.

Amongst others, the substituants can be selected amongst —OH and —OR with R representing a linear, branched or cyclic, saturated or unsaturated hydrocarbon radical having 1 to 6 carbon atoms, optionally being halogenated, even perhalogenated.

More preferably, the $R_2$ radical represents a methyl, ethyl, propyl, isopropyl, n-butyl, ter-butyl or isobutyl radical.

Preferably, the $R_3$ radical represents a radical of the formula —$C_6H_{(5-y')}$—$B_{y'}$ where y'=1, 2 or 3; or a radical of the formula -A-$C_6H_{(5-y)}$—$B_y$ where y=0, 1 or 2.

Preferably, A is a linear or branched, saturated or unsaturated hydrocarbon divalent radical having 1 to 12 carbon atoms, optionally substituted.

The substituants for A are preferably selected amongst -Hal (halogen, even perhalogen); —CN; —COOR; —NO$_2$; —SO$_2$—OR; with R representing a linear, branched or cyclic, saturated or unsaturated hydrocarbon radical having 1 to 6 carbon atoms, optionally being halogenated, even perhalogenated.

Preferably, B is a linear or branched, saturated or unsaturated hydrocarbon radical having 1 to 12 carbon atoms, optionally substituted.

The substituants for B are preferably selected amongst -Hal (halogen, even perhalogen); —CN; —COOR; —NO$_2$; —SO$_2$—OR; with R representing a linear, branched or cyclic, saturated or unsaturated hydrocarbon radical having 1 to 6 carbon atoms, optionally being halogenated, even perhalogenated, More preferably, the $R_3$ radical is a group selected amongst one of the following formulae:

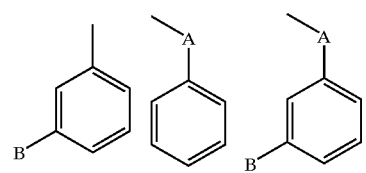

-continued

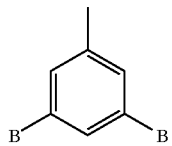

where A and B have the meanings as hereabove.

More particularly, the divalent A radical can be a methylene, an ethylene, a propylene.

The B radical is preferably a methyl, ethyl, propyl or isopropyl radical, substituted by one or more halogens, more particularly chlorine, bromine, iodine or fluorine, and more preferably completely halogenated (perhalogenated) such as perfluoridated. The most preferred one is in particular the perfluoromethyl radical (—$CF_3$).

More preferably, the X radical represents a radical selected amongst —OH or —$OR_4$ with $R_4$ representing a linear, cyclic or branched, saturated or unsaturated hydrocarbon radical having 1 to 6 carbon atoms, optionally substituted.

The substituants can be selected amongst —OH and —OR with R representing a linear, branched or cyclic, saturated or unsaturated hydrocarbon radical having 1 to 6 carbon atoms, optionally being halogenated, even perhalogenated.

More preferably, the X radical represents a radical selected amongst —OH, —$OCH_3$, —$OC_2H_5$, —O—$C_3H_7$ or —$OC_4H_9$.

The particularly preferred compounds include:
{2-[acetyl-(3-trifluoromethyl-phenyl)-amino]-3-méthyl-butyrylamino}acetic acid,
{2-[acetyl-(3-trifluoromethyl-phenyl)-amino]-3-máthyl-butyrylamino}ethyl acetate,
[2-(acetyl-benzyl-amino)-3-méthyl-butyrylamino]acetic acid,
[2-(acetyl-benzyl-amino)-3-méthyl-butyrylamino]ethyl acetate, and
[2-{benzyl-[(diethoxy-phosphoryl)-acetyl]-amino}-3-méthyl-butyryl-amino]ethyl acetate.

The compounds according to the Invention can be easily prepared by the man of the art based on its general knowledge. It is more particularly possible to react together a carboxylic acid, an aldehyde, an amino compound and an isonitrile, according to Ugi reaction.

Obviously, upon the synthesis of the compounds according to the invention and depending on the nature of the various radicals present on the starting compounds, the man of the art will make sure to protect some substituants so that they are not involved in the reaction sequence.

The compound quantity to be used in the compositions according to the invention can be easily determined by the man of the art, depending on the nature of the compound to be used, on the person to be treated and/or the desired effect. Generally, this amount can range from 0.00001 to 20% by weight based on the total weight of the composition, preferably 0.001 to 10% by weight.

Preferred Anti-Inflammatory Compounds

It is meant by "compound" or anti-inflammatory "agent" according to the invention particularly an antagonist compound of the inflammatory cytokines. An antagonist of the inflammatory cytokines is a compound adapted to inhibit the synthesis and/or the release of one or more inflammatory cytokines. Are also included in the definition of an antagonist of the inflammatory cytokines, the compounds inhibiting or blocking the cytokine attachment to their receptor(s).

The preferred anti-inflammatory compounds according to the invention are antagonist compounds of IL-1, IL-8, TNFα and TNFβ.

Are included amongst the antagonists of the inflammatory cytokines, according to the invention, the Lys-Pro-Vat (KPV) tripeptide and all αMSH derivatives, all the Inhibitors of the cytokine release (therapeutic class of CSAID for cytokine suppressive anti-inflammatory drugs), the substituted N-oxide pyrimidine family (EP 99 401 719.2, priority FR 9809509) and the A4 lipoxin inductors (EP 99 402 771.2, priority FR 9814211), alga extracts adapted to modulate the cytokine production by keratinocytes such as Phycosaccharide® sold by CODIF corporation, Phlorogine® sold by SECMA corporation, *Aloe vera* or *Gingko biloba* or also *Rose gallica* extracts; the natural antagonist to IL-1 (IL-1RA).

According to the invention, the anti-inflammatory compound or agent can also be selected amongst steroidal (hydrocortisone, betamethasone, dexamethasone, etc.) or non steroidal anti-inflammatory products, such as aspirin or paracetamol.

According to the invention, the anti-inflammatory derivative can also be selected amongst proinflammatory neuropeptide antagonists (antagonist of P substance, antagonist GCRP (for calcitonin gene related peptide), bradykinin antagonist) even some MAE (exciting amino acids) antagonists.

The anti-inflammatory compounds or agents are preferably present in the compositions according to the Invention at a concentration ranging from 0.00001 to 10% by weight approximately based on the total weight of the composition, More preferably, the anti-inflammatory compound concentration can range from 0.0005 to 2% by weight based on the total weight of the composition.

The compounds of the formula (I) can more particularly be used in a composition comprising a physiologically acceptable medium, more particularly in a cosmetic or pharmaceutical composition which comprises therefore additionally a cosmetically or pharmaceutically acceptable medium.

The physiologically acceptable medium In which the compounds according to the invention can be used, as well as the components thereof, their amount, the galenic form of the composition and its preparation mode, can be selected by the man of the art on the basis of its general knowledge depending on the type of the desired composition.

Generally, such a medium can be anhydrous or aqueous. It can thus comprise an aqueous phase and/or a fatty phase, even be Incorporated into more complex emulsions such as triple emulsions (for example, water in oil in water).

The association of at least one N-acylamino-amide compound and at least one anti-inflammatory compound can be used, more particularly, alone or in a mixture, in a composition comprising a physiologically acceptable medium, in particular in a cosmetic or pharmaceutical composition which, therefore, comprises a cosmetically or pharmaceutically acceptable medium.

The physiologically acceptable medium in which the compounds according to the invention can be used, as well as the constituents thereof, their amount, the galenic form of the composition and its preparation mode, can be selected by the man of the art on the basis of its general knowledge depending on the type of the desired composition.

Generally, this medium can be anhydrous or aqueous. It can thus comprise an aqueous phase and/or a fatty phase.

For applying onto the skin, the composition can have the form in particular of an aqueous or an oily solution; of a dispersion of the lotion or serum type; of emulsions of liquid or semi-liquid consistency of the milk type obtained through dispersion of a fatty phase into an aqueous phase (O/W) or reversely (W/O); of suspensions or emulsions of a soft consistency of the cream type or aqueous or anhydrous gel type; of microcapsules or microparticles; of vesicular dispersions of the ionic and/or non ionic type.

For applying on the hair, the composition can be in the form of aqueous, alcoholic or hydroalcoholic solutions; in the form of creams, gels, emulsions, foams; in the form of aerosol compositions comprising a pressurized propellant as well.

When the composition is in an aqueous form, in particular in an aqueous dispersion, emulsion or solution, it can comprise an aqueous phase, which may comprise water, flower water and/or mineral water.

Said aqueous phase can additionally comprise alcohols such as $C_1$–$C_6$ monoalcohols and/or polyols such as glycerol, butyleneglycol, isoprene glycol, propyleneglycol, polyethyleneglycol.

When the composition according to the invention is in the form of an emulsion, it can optionally additionally comprise a surfactant, preferably in an amount ranging from 0.01 to 30% by weight based on the total weight of the composition. The composition according to the invention can also comprise at least one co-emulsifier which can be selected amongst oxyethylenated sorbitan monostearate, fatty alcohols such as stearyl alcohol or cetyl alcohol, or esters of fatty acids and polyols such as glyceryl stearate.

The composition according to the invention can also comprise a fatty phase, in particular made of fatty bodies liquid at 25° C., such as oils from animal, vegetable, mineral or synthetic origin, either volatile or not; fatty bodies solid at 25° C. such as waxes from animal, vegetable, mineral or synthetic origin; of pasty fatty bodies; of gums; and the mixtures thereof, The volatile oils are generally oils having, at 25° C., a saturating vapor tension at least equal to 0.5 millibar (50 Pa).

Are included amongst the fatty phase components:
cyclic volatile silicones having 3 to 8 silicon atoms, preferably 4 to 6,
cyclocopolymers of the dimethylsiloxane/methylalkylsiloxane type,
linear volatile silicones with 2 to 9 silicon atoms,
hydrocarbon volatile oils, such as isoparaffins and, more particularly, isododecane and fluorinated oils,
poly($C_1$–$C_{20}$)alkylsiloxanes and, more particularly, those with trimethylsilyl end groups, amongst which linear polydimethylsiloxanes and alkylmethylpolysiloxanes such as cetyidimethicone (so-called CTFA),
silicones modified by aliphatic and/or aromatic groups, optionally fluorinated, or by functional groups such as hydroxyl, thiol and/or amine groups,
phenylated silicone oils,
oils from animal, vegetable or mineral origin, in particular animal or plants oils made of esters of fatty acids and polyols, in particular liquid triglyceride, for example sunflower, corn, soya, marrow, grape seed, sesame, hazelnut, apricot, almond, or avocado oils; fish oils, glycerol tricaprocaprylate, or plant or animal oils having the formula $R_1COOR_2$, where $R_1$ represents the residue of a superior fatty acid having 7 to 19 carbon atoms, and $R_2$ represents a branched hydrocarbon chain having 3 to 20 carbon atoms, for example Purcellin oil; paraffin oil, liquid paraffin, perhydrosqualene, wheatgerm, calophyllum, sesame, macadamia, grape seed, colza, copra, arachis, palm, castor, jojoba, olive or cereal germ oils; fatty acid esters; alcohols; acetylglycerides; octanoates, decanoates or ricinoleates from alcohols or polyalcohols; fatty acid triglycerids; glycerids;
fluorinated and perfluorinated oils
silicone gums;
waxes from animal, vegetable, mineral or synthetic origin, such as microcrystalline waxes, paraffin, petrolatum, liquid paraffin, ozokerite, Montan wax; beeswax, lanolin and the derivatives thereof; Candelilla, Ouricury and Japan waxes, cocobutter, cork fibre or sugar cane waxes; hydrogenated oils solid at 25° C., ozokerites, fatty esters and glycerides solid at 25° C.; polyethylene waxes and waxes obtained through Fischer-Tropsch synthesis; hydrogenated oils solid at 25° C.; lanolins; fatty esters solid at 25° C.; silicone waxes; fluorinated waxes.

As it is known, the composition according to the invention can comprise the usual builders in the field being involved, such as hydrophilic or lipophilic gelling agents, hydrophilic or lipophilic additives, actives, in particular hydrophilic or lipophilic cosmetic or pharmaceutical actives, preservatives, antioxidants, solvents, perfumes, fillers, pigments, nacres, UV filters, odor absorbers and colorants, Such builders, depending on their nature, can be introduced into the fatty phase, into the aqueous phase and/or into lipid spherules.

The nature and the amount of such builders can be selected by the man of the art, based on its general knowledge, so as to obtain the desired presentation form for the composition. Anyway, the man of the art will make sure to select all the optional complementary compounds and/or their amount, so that the advantageous properties of the composition according to the invention are not, or substantially not, altered by the contemplated addition.

The cosmetic or pharmaceutical compositions according to the invention can, in particular, have the form of a composition designed for caring and/or treating ulcerated areas or which have been subjected to a cutaneous stress or microstress, in particular generated by an exposure to the UV and/or the contact with an irritating product.

Accordingly, the compositions according to the invention can, in particular, exhibit the form of:
a care, treatment, cleaning or protection product for the face or the body skin, including the scalp, such as a (day, night, hydrating) care composition for the face or the body; an anti-wrinkle or anti-ageing composition for the face; a mating composition for the face; a composition for the irritated skins; a makeup removing composition; a body milk, in particular being hydrating optionally an after-sun body milk;
a sun protective, artificial sun tanning (self-tanning) or after-sun care composition;
a capillary composition, more particularly a sun protective cream or gel; a scalp care composition, including an hair restoring or hair growth composition; an anti-parasitic shampoo;
a face skin, body or lip make-up product, such as a foundation cream, a tinted cream, a cheek or eye-lid make-up product, a free or compact powder, an anti eye-ring stick, a concealing stick, a lipstick, a lip care product; and
a mouth hygiene product, such as a tooth-paste or a mouth-wash lotion.

The compositions according to the invention find a preferred application as a composition for face skin care, of the anti-wrinkle or anti-ageing type and as a sun protective or an after-sun composition.

The object of the present invention is also to provide a method comprising the steps of cosmetically treating the body or the face skin, In particular, the scalp, wherein a cosmetic composition is applied onto the skin, comprising an association between a compound of the N-acylaminoamide family and at least an anti-inflammatory agent, leaving it in contact and optionally rinsing.

The cosmetic treatment method according to the invention can be applied in particular by applying cosmetic compositions such as defined hereabove, according to the usual use technique of said compositions. For example application of creams, gels, serums, lotions, makeup removing milks or anti-sun compositions on the skin or on dry hair; application of a scalp lotion on wet hair, application of tooth-paste on the gums.

The invention is illustrated in further detail in the following examples.

EXAMPLE 1

Preparation of {2-[acetyl-(3-trifluoromethyl-phenyl)-amino]-3-méthyl-butyrylamino}ethyl acetate of the formula:

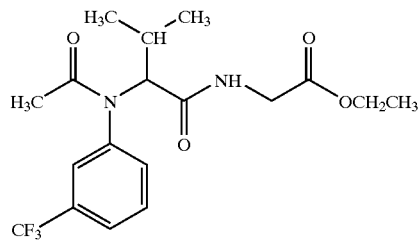

0.63 ml isobutyraldehyde and 1 ml trifluoromethylamine (1.15 eq) are mixed in 15 ml methanol under stirring. It is left to react for 15 minutes at 20° C., thereafter 0.46 ml acetic acid are added (1.15 eq) and it is left to react for 10 minutes at 20° C. Then 0.8 ml 95% ethyl isocyanoacetate (1 eq) are added and left to react for 48 hours at 20° C.

The reaction medium is concentrated using a rotovapor and the residue is purified on a silica column (eluant: heptane:3/ethyl acetate: 7; Rf=0.5).

2.45 g of a compound in the form of a waxy solid are obtained, whence a 91% yield.

RMN$^1$H (200 MHz; CDC13) δ ppm: 0.9 (6H; q), 1.3 (3H; t), 1.8 (3H; s), 2.3 (1H; m), 4.0 (2H, q), 4.2 (2H; q), 4.4 (2H; d), 7.3 (1H; t), 7.5 (4H; m).

EXAMPLE 2

Preparation of {2-[acetyl-(3-trifluoromethyl-phenyl)-amino]-3-méthyl-butyrylamino}acetic acid of the formula

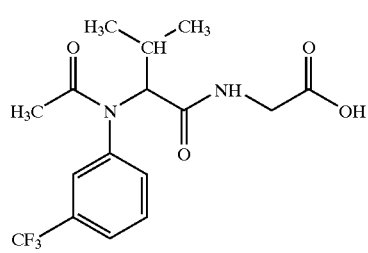

2 g of the compound prepared according to example 1 are solubilized in 30 ml acetone. 30 ml 2N sodium hydroxyde are added and left to react for 6 hours at 20° C. The reaction medium is concentrated using a rotovapor. The residual aqueous phase is acidified at pH 2 adding concentrated HCl and then extracted with $CH_2Cl_2$.

The organic phase is dry concentrated after drying on sodium sulfate.

A residue is obtained which is solubilized with a base water mixture at 10% ethanol and then again acidified with concentrated HCl at pH 2.; A new extraction by $CH_2Cl_2$ is performed, the organic phase is dried on sodium sulfate, filtered and dry concentrated under vacuum in a rotovapor.

1.3 g of a compound are obtained in the form of a slight light brown solid, whence a 70% yield.

RMN$^1$H (200 MHz; DMSO) δ ppm: 0.9 (6H; q), 3.7 (2H; m), 1.8 (4H; m), 4.8 (2H; d), 7.6 (4H, q), 8.4 (1H; t), 12.5 (1H; s).

EXAMPLE 3

The anti-elastasic activity of compounds according to the invention is determined in vitro compared to the human leukocyte elastase (ELH).

The test is performed in the following way:

A Me-OSAAPV-p-NA (methyl-O-succinate alanine alanine proline valine-p-nitroaniline) substrate, onto which ELH (40 milli-units per ml) and 0.1% of the compound to be tested are applied, is left for incubating at 37° C. for 60 minutes.

Thereafter, the % inhibition of the control elastase activity is determined by spectrophotometry.

The tested compounds are the following:
Compound A: {2-[acetyl-(3-trifluoromethyl-phenyl)-amino]-3-méthyl-butyryl-amino}acetic acid,
Compound B: (2-{benzyl-[(diéthoxy-phosphoryl)-acetyl]-amino}-3-méthyl-butyryl-amino)ethyl acetate,
Compound C: [2-(acetyl-benzyl-amino)-3-méthyl-butyrylamino]acetic acid,
Compound D: [2-(acetyl-benzyl-amino)-3-méthyl-butyrylamino]ethyl acetate.

The following results are obtained:

| Compound (concentration: 0.1%) | % Inhibition of the control elastase activity |
|---|---|
| Compound A | 67% |
| Compound B | 17% |
| Compound C | 20% |
| Compound D | 13% |

The same way, the inhibition % of the control elastase activity is determined for compound A, at various concentrations.

The following results are obtained:

| Compound A concentration | % Inhibition of the control elastase activity |
|---|---|
| 0.01% | 53% |
| 0.05% | 50% |
| 0.1% | 68% |
| 0.2% | 68% |

Compound A therefore generates a strong inhibition of the elastase activity, even in a small amount.

EXAMPLE 4

The ex vivo activity of example 2 compound has been evaluated on surviving human skins treated by a human leukocyte elastase (ELH).

The test is performed the following way.

Fresh human skin cuts from two different donors are treated for 2 hours, at 20° C., by 20 µl of a buffer solution (pH 7.4) optionally comprising 10 µg/ml ELH and optionally 0.1% of the compound to be tested, optionally previously put in solution in ethanol.

The elastic fibres are colored in blue using catechin (+) and quantified morphometrically using a computer assisted image analysis. The average derma surface percentage occupied by elastic fibres Is evaluated this way.

The following results are obtained:

|  | % Surface occupied by elastic fibres | |
| --- | --- | --- |
|  | Skin 1 | Skin 2 |
| Control (untreated skin) | 12.7% | 15.25% |
| ELH treated skin | 4.85% | 6.85% |
| ELH treated skin + example 2 compound | 13.95% | 11.85% |

It is therefore found out that the compound according to the invention generates a skin significative protection against the destruction of elastic fibres induced by elastase.

EXAMPLE 5

The ex vivo activity of example 2 compound has been evaluated on surviving human skins treated by a human leukocyte elastase (ELH).

The test is performed the following way.

Fragments of normal human skin from three different donors are deposited in inserts positioned in culture wells. Culture medium added with antibiotics is added in the bottom of the wells. A pass is performed through slow diffusion between the two compartments via a porous membrane (pore size: 12 µm).

The culture medium is renewed every three days.

On the skin fragments, optionally 0.5 µg ELH per ml culture medium are added.

5 µl of the compound to be tested are also added every two days, previously put in solution at 0.2% by weight in ethanol.

The skins are kept surviving for 10 days at 37° C.

The elastic fibres are colored in blue using catechin (+) and quantified morphometrically using a computer assisted image analysis, The average derma surface percentage occupied by elastic fibres is evaluated this way.

The following results are obtained:

|  | % Surface occupied by elastic fibres |
| --- | --- |
| Control (untreated skin) | 7.4% |
| ELH treated skin | 5.1% |
| ELH treated skin + example 2 compound | 7.1% |

It is therefore found out that the compound according to the invention generates a significant skin protection against the destruction of elastic fibres induced by the elastase.

EXAMPLE 6

The activity of the example 2 compound has been evaluated on surviving human skins irradiated by UVA (8 J/cm$^2$).

The test is performed the following way.

Fragments of normal human skin from four different donors are deposited in inserts positioned in culture wells. Culture medium added with antibiotics is added in the bottom of the wells. A pass is performed through slow diffusion between the two compartments via a porous membrane (pore size: 12 µm).

The culture medium is renewed every three days.

On the skin fragments, every two days, 5 µl of the compound to be tested are added, previously put in solution at 0.2% wt in ethanol.

The skins are kept surviving for 7 days at 37° C.

The skins are radiated once at 8 J/cm$^2$ (RMX-3W Vilbert-Lourmat lamp).

The elastic fibres are colored in blue using catechin (+) and quantified morphometrically using a computer assisted image analysis. The average derma surface percentage occupied by elastic fibres is evaluated this way.

The following results are obtained;

|  | Elastic fibres morphometric analysis (superficial derma) | Collagen morphometric analysis (superficial derma) |
| --- | --- | --- |
| Untreated skin | 6.75% | 87% |
| UVA treated skin (8 J/cm$^2$) | 3.9% | 81% |
| UVA treated skin (8 J/cm$^2$) + compound | 6.8% | 92% |

It is found out that the compound according to the invention does have an activity towards the destruction of elastic fibres in the UVA radiated skin superficial derma.

This compound also exhibits an adequate effect on the collagen protection.

EXAMPLE 7

Composition for Topic Application

| 4-N-alkyl pyrimidine N-oxide | 0.1% |
| --- | --- |
| Example 1 compound | 1% |
| Propylene glycol isostearate | 13% |
| Polyethylene glycol (8 OE) | 5% |
| Propylene glycol | 3% |
| Pentylene glycol | 3% |
| Glyceryl stearate and polyethylene glycol stearate (100 OE) | 5% |
| Oxyethylenated (20 OE) sorbitan monostearate | 0.5% |
| Oxypropylenated (5 OP) oxyethylenated (20 OE) cetyl alcohol | 1% |
| Gelling agents | 0.5% |
| $C_{12}$–$C_{15}$ alkyl benzoates | 4% |
| Ethanol | 3% |
| Sodium hydroxide | 0.12% |
| Preservatives | qs |
| Water | qsp 100% |

EXAMPLE 8

Composition for Topic Application

The following emulsion is prepared conventionally (% by weight):

| | |
|---|---|
| Hydrocortisone | 0.1% |
| Example 1 compound | 1% |
| Propylene glycol isostearate | 13% |
| Polyethylene glycol (8 OE) | 5% |
| Propylene glycol | 3% |
| Pentylene glycol | 3% |
| Glyceryl stearate and polyethylene glycol stearate (100 OE) | 5% |
| Oxyethylenated (20 OE) sorbitan monostearate | 0.5% |
| Oxypropylenated (5 OP) oxyethylenated (20 OE) cetyl alcohol | 1% |
| Gelling agents | 0.5% |
| $C_{12}$–$C_{15}$ alkyl benzoates | 4% |
| Ethanol | 3% |
| Sodium hydroxide | 0.12% |
| Preservatives | qs |
| Water | qsp 100% |

EXAMPLE 9

Face Care Cream

The following oil-in-water emulsion is prepared conventionally (% by weight):

| | |
|---|---|
| Example 2 compound | 1% |
| Glycol stearate | 2% |
| Polysorbate 60 (Tween 6O ® sold by ICI corporation) | 1% |
| Stearic acid | 1.4% |
| Triethanolamine | 0.7% |
| Carbomer | 0.4% |
| Shea butter liquid fraction | 12% |
| Perhydrosqualene | 12% |
| *Rosa gallica* extract | 1% |
| Antioxidant | qs |
| Perfume | qs |
| Preservative | qs |
| Water | qsp 100% |

EXAMPLE 10

Face Milk

Following milk is prepared conventionally (% by weight):

| | |
|---|---|
| Liquid paraffin | 7% |
| Example 2 compound | 1% |
| Glyceryl monostearate, polyethylene glycol stearate (100 OE) | 3% |
| Carboxyvinyl polymer | 0.4% |
| Stearyl alcohol | 0.7% |
| Soya protein | 3% |
| NaOH | 0.4% |
| LPV tripeptide | 0.001% |
| Preservative | qs |
| Water | qsp 100% |

EXAMPLE 11

Hair Restoring Lotion

The following lotion is prepared conventionally (% by weight):

| | |
|---|---|
| Example 1 compound | 1% |
| Propylene glycol | 23% |
| Ethanol | 55% |
| Minoxidil | 2% |
| Hydrocortisone | 0.1% |
| Water | qsp 100% |

This lotion can be applied onto the scalp of alopecic people for preventing the UV effect, before and/or after sun exposure.

EXAMPLE 12

Hair Restoring Lotion

The following lotion is prepared conventionally (% by weight):

| | |
|---|---|
| Example 2 compound | 1% |
| Propylene glycol | 23% |
| Ethanol | 55% |
| Aminexil | 1.5% |
| LPV tripeptide | 0.0005% |
| Water | qsp 100% |

This hair restoring lotion can be applied onto the scalp of alopecic people.

What is claimed is:

1. A cosmetic or dermatological composition comprising an N-acylaminoamide compound elastase inhibitor and at least one anti-inflammatory compound, wherein the N-acylaminoamide compound is a compound of the formula (I):

$$\underset{R_1}{\overset{Y}{\|}}{\underset{|}{\overset{|}{C}}}-\underset{R_3}{\overset{R_2}{\underset{|}{N}}}-\underset{}{\overset{}{C}H}-\underset{\|}{\overset{O}{C}}-NH-CH_2-X \qquad (I)$$

where:

Y represents O or S, $R^1$ represents:
(i) a hydrogen atom,
(ii) a linear, branched or cyclic, saturated or unsaturated hydrocarbon radical having 1 to 18 carbon atoms, optionally substituted by 1 to 5 groups, either identical or different, selected from —OH; —OR; —O—COR; —SH; —SR; —S—COR; —NH$_2$; —NHR; —NRR'; —NH—COR; halogen; —CN; —COOR; —COR; —P(O)—(OR)$_2$; —SO$_2$—OR; with R and R' representing, independently from each other, a linear, branched or cyclic, saturated or unsaturated hydrocarbon radical having 1 to 6 carbon atoms, optionally being halogenated;

said R and R' radicals being able to form together with N a carbon ring with 5 to 6 ring members optionally comprising further at least one heteroatom being selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical, having 1 to 6 carbon atoms, optionally being halogenated;

(iii) a radical selected from —OR; —NH$_2$; —NHR; —NRR'; —NH—COR; —COOR; —COR; with R and R' representing, independently from each other, a linear, branched or cyclic, saturated or unsaturated hydrocarbon radical having 1 to 6 carbon atoms, optionally being halogenated, said R and R' radicals being able to form together with N a carbon ring with 5 to 6 ring members optionally comprising, additionally, at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical having 1 to 6 carbon atoms, optionally being halogenated;

the $R^2$ radical represents a linear, branched or cyclic, saturated or unsaturated hydrocarbon radical, with 1 to 18 carbon atoms, optionally substituted by 1 to 5 groups, either identical or different, selected from —OH; —OR; —O—COR; —SH; —SR; —S—COR; —NH$_2$; —NHR; —NRR'; —NH—COR; halogen; —CN; —COOR; —COR; with R and R' representing, independently from each other, a linear, branched or cyclic, saturated or unsaturated hydrocarbon radical, with 1 to 6 carbon atoms, optionally halogenated; said R and R' radicals able to form together with N a carbon cycle with 5 to 6 chains optionally comprising, additionally, at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical, with 1 to 6 carbon atoms, optionally halogenated;

the $R^3$ radical represents a radical selected from those of formulae (II) or (III):

-A-C$_6$H$_{(5-y)}$—B$_y$   (II)

—C$_6$H$_{(5-y')}$—B$_{y'}$   (III)

where:
y is an integer between 0 and 5 inclusive, and y' is an integer between 1 and 5 inclusive;

A is a linear or branched, saturated or unsaturated hydrocarbon divalent radical, with 1 to 18 carbon atoms, optionally being substituted by 1 to 5 groups, either Identical or different, selected from —OH; —OR; —O—COR; —SH; —SR; —S—COR; —NH$_2$; —NHR; —NRR'; —NH—COR; halogen; —CN; —COOR; —COR; —NO$_2$; —SO$_2$OR;

with R and R' representing, independently from each other, a linear, branched or cyclic, saturated or unsaturated hydrocarbon radical, with 1 to 6 carbon atoms, optionally being halogenated;

said R and R' radicals being able to form together with N a carbon ring with 5 to 6 ring members optionally comprising further at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical having 1 to 6 carbon atoms, optionally being halogenated;

B is a linear or branched, saturated or unsaturated hydrocarbon radical having 1 to 18 carbon atoms, optionally substituted by 1 to 5 groups, either identical or different, selected from —OH; —OR; —O—COR; —SH; —SR; —S—COR; —NH$_2$; —NHR; —NRR'; —NH—COR; Halogen; perhalogen; —CN; —COOR; —COR; —NO$_2$; —SO$_2$OR; with R and R' representing, independently from each other, a linear, branched or cyclic, saturated or unsaturated hydrocarbon radical having 1 to 6 carbon atoms, optionally being halogenated;

said R and R' radicals being able to form together with N a carbon ring with 5 to 6 ring members optionally comprising further at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon having 1 to 6 carbon atoms, optionally being halogenated;

the X radical is a radical selected from —OH; —OR$_4$; —NH$_2$; —NHR$_4$; —NR$_4$R$_5$; —SR$_4$; —COOR$_4$; —COR$_4$;

with R$_4$ and R$_5$ representing, independently from each other, a linear, cyclic or branched, saturated or unsaturated hydrocarbon radical having 1 to 6 carbon atoms, optionally substituted by 1 to 5 groups, identical or different, selected from —OH; —OR; —O—COR; —SH; —SR; —S—COR; —NH$_2$; —NHR; —NH—COR; Halogen; perhalogen; —CN; —COOR; —COR; with R and R' representing, independently from each other, a linear, branched or cyclic, saturated or unsaturated hydrocarbon radical having 1 to 6 carbon atoms, optionally being halogenated; said R and R' radicals being able to form together with N a carbon ring with 5 to 6 ring members optionally comprising further at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical having 1 to 6 carbon atoms, optionally being halogenated;

said R$_4$ and R$_5$ radicals being able to form together with N a carbon ring with 5 to 6 ring members optionally comprising further at least one heteroatom selected from O, N and/or S in the ring and/or optionally substituted by 1 to 5 groups, identical or different, selected from —OH; —OR"; —O—COR"; —SH; —SR"; —S—COR"; —NH$_2$; —NHR"; —NH—COR"; halogen; —CN; —COOR"; —COR"; with R" representing a linear, branched or cyclic, saturated or unsaturated hydrocarbon radical having 1 to 6 carbon atoms, optionally being halogenated;

the mineral or organic acid salts thereof, the optical isomers thereof, in an isolated form or as a racemic mixture.

2. A composition according to claim 1, wherein the compound of formula (I) is such that:

Y represents oxygen, and/or $R_1$ represents hydrogen or a linear or branched, saturated or unsaturated hydrocarbon radical having 1 to 12, carbon atoms, optionally substituted, and/or the $R_1$ substituents are selected from —OH; —OR; and/or —P(O)—(OR)$_2$ with R representing a linear, branched or cyclic, saturated or unsaturated hydrocarbon radical having 1 to 6 carbon atoms, optionally being halogenated; and/or the $R_2$ radical represents a linear, branched or cyclic, saturated or unsaturated hydrocarbon radical having 1 to 12 carbon atoms, optionally substituted, and/or the $R_2$ substituents are selected from —OH and —OR with R representing a linear, branched or cyclic, saturated or unsaturated hydrocarbon radical having 1 to 6 carbon atoms, optionally being halogenated; and/or the $R_3$ radical represents a radical of the formula —C$_6$H$_{(5-y')}$—B$_{y'}$' where y'=1, 2 or 3; or a radical of the formula -A-C$_6$H$_{(5-y)}$—B$_y$ where y=0, 1 or 2; and/or the A radical of $R_3$ is a linear or branched, saturated or unsaturated hydrocarbon divalent radical having 1 to 12 carbon atoms, optionally substituted; and/or the B radical of $R_3$ is a linear or branched, saturated or unsaturated hydrocarbon radical having 1 to 12 carbon atoms, optionally substituted; and/or the substituents for A and/or for B are selected from Halogen; perhalogen; —CN; —COOR; —NO$_2$; —SO$_2$—OR; with R representing a linear, branched or cyclic, saturated or unsaturated hydrocarbon radical having 1 to 6 carbon atoms, optionally being halogenated and/or the X radical represents a radical selected from —OH or —OR$_4$ with $R_4$ representing a linear, cyclic or branched, saturated or unsaturated hydrocarbon radical having 1 to 6 carbon atoms, optionally substituted, and/or the $R_4$ substituents of X are selected from —OH or —OR with R representing a linear, cyclic or branched, saturated or unsaturated hydrocarbon radical having 1 to 6 carbon atoms, optionally being substituted.

3. A composition according to claim 1, wherein the compound of the formula (I) is such that:

the $R_1$ radical represents a methyl, ethyl, propyl or isopropyl radical, optionally substituted by a —OH or —P(O)—(OH)$_2$ group with R representing methyl, ethyl, propyl or isopropyl; and/or the $R_2$ radical represents a methyl, ethyl, propyl, isopropyl, n-butyl, ter-butyl or isobutyl radical; and/or the $R_3$ radical represents a group selected from one of the following formulae:

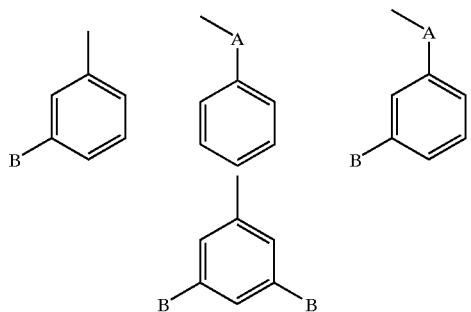

where the divalent A radical is a methylene, ethylene, propylene and/or the B radical is a methyl, ethyl, propyl or isopropyl radical, substituted by one or more halogens, the X radical represents a radical selected from —OH, —OCH$_3$, —OC$_2$H$_5$, —O—C$_3$H$_7$ or OC$_4$H$_9$.

4. A composition according to claim 1, wherein the N-acylaminoamide compound is selected from the group consisting of the following compounds:

{2-[acetyl-(3-trifluoromethyl-phenyl)-amino]-3-methyl-butyrylamino}acetic acid,

{2-[acetyl-(3-trifluoromethyl-phenyl)-amino]-3-methyl-butyrylamino}ethyl acetate,

[2-(acetyl-benzyl-amino)-3-methyl-butyrylamino]acetic acid,

[2-(acetyl-benzyl-amino)-3-methyl-butyrylamino]ethyl acetate, and (2-{benzyl-[(diethoxy-phosphoryl)-acetyl]-amino}-3-methyl-butyryl-amino]ethyl acetate.

5. A composition according to claim 1, wherein the N-acylaminoamide compound is present in an amount ranging from 0.00001 to 20% by weight based on the total weight of the composition.

6. A composition according to claim 5 wherein the N-acylaminoamide compound is present in an amount ranging from 0.0001 to 10% by weight.

7. A composition according to claim 1, wherein the anti-inflammatory compound is selected from the group consisting of the Lys-Pro-Val tripeptide and derivatives of αMSH.

8. A composition as claimed in claim 1, wherein the anti-inflammatory compound is present in an amount ranging from 0.00001 to 10% by weight based on the total weight of the composition.

9. A composition as claimed in claim 8, wherein the anti-inflammatory compound is present in an amount ranging from 0.00005 to 2% by weight.

10. A composition as claimed in claim 1, comprising an effective amount of said inhibitor and said compound for caring and/or treating ulcerated areas or areas having been subjected to a cutaneous stress or microstress.

11. A composition according to claim 1, in the form of:

a care, treatment, cleaning or protection product, of the face or the body skin, including the scalp, a sun protective, artificial sun tanning or after-sun care composition;

a capillary composition or a scalp care composition, a face skin, body or lip make-up product, or a mouth hygiene product.

12. A composition according to claim 1, in the form of an anti-wrinkle, anti-ageing, sun protective or after-sun face skin care composition.

13. A cosmetic or dermatological composition comprising an N-acylaminoamide compound elastase inhibitor and at least one anti-inflammatory compound, wherein the N-acylaminoamide compound is a compound of the formula (I):

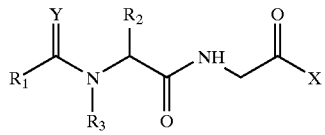
(I)

where:
- Y represents oxygen,
- $R_1$ represents hydrogen or a linear or branched, saturated or unsaturated hydrocarbon radical having 1 to 12 carbon atoms, optionally substituted,
- the $R_1$ substituents are selected from —OH; —OR; and/or —P(O)—(OR)$_2$ with R representing a linear, branched or cyclic, saturated or unsaturated hydrocarbon radical having 1 to 6 carbon atoms, optionally being halogenated;
- the $R_2$ radical represents a linear, branched or cyclic, saturated or unsaturated hydrocarbon radical having 1 to 12 carbon atoms, optionally substituted, and/or
- the $R_2$ substituents are selected from —OH and —OR with R representing a linear, branched or cyclic, saturated or unsaturated hydrocarbon radical having 1 to 6 carbon atoms, optionally being halogenated;
- the $R_3$ radical represents a radical of the formula —C$_6$H$_{(5-y')}$—B$_{y'}$ where y'=1, 2 or 3; or a radical of the formula -A-C$_6$H$_{(5-y)}$—B$_y$ where y=0, 1 or 2;
- the A radical of $R_3$ is a linear or branched, saturated or unsaturated hydrocarbon divalent radical having 1 to 12 carbon atoms, optionally substituted; and/or
- the B radical of $R_3$ is a linear or branched, saturated or unsaturated hydrocarbon radical having 1 to 12 carbon atoms, optionally substituted;
- the substituents for A and/or for B are selected from Halogen; perhalogen; —CN; —COOR; —NO$_2$; —SO$_2$—OR; with R representing a linear, branched or cyclic, saturated or unsaturated hydrocarbon radical having 1 to 6 carbon atoms, optionally being halogenated; and
- the X radical represents a radical selected from —OH or —OR$_4$ with R$_4$ representing a linear, cyclic or branched, saturated or unsaturated hydrocarbon radical having 1 to 6 carbon atoms, optionally substituted.

14. A cosmetic or dermatological composition comprising an N-acylaminoamide compound elastase inhibitor and at least one anti-inflammatory compound, wherein the N-acylaminoamide compound is a compound of the formula (I):

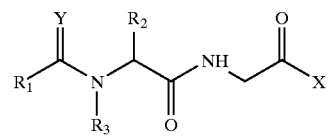
(I)

where:
- the $R_1$ radical represents a methyl, ethyl, propyl or isopropyl radical, optionally substituted by a —OH or —P(O)—(OH)$_2$ group with R representing methyl, ethyl, propyl or isopropyl;
- the $R_2$ radical represents a methyl, ethyl, propyl, isopropyl, n-butyl, ter-butyl or isobutyl radical;
- the $R_3$ radical represents a group selected from one of the following formulae:

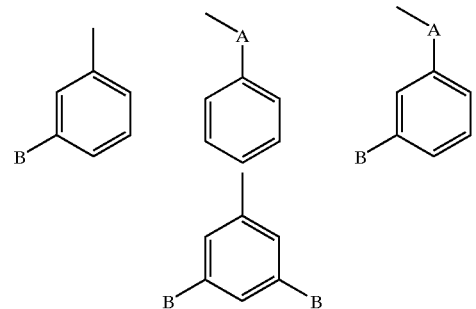

where the divalent A radical is a methylene, ethylene, propylene and/or the B radical is a methyl, ethyl, propyl or isopropyl radical, substituted by one or more halogens, and the X radical represents a radical selected from —OH, —OCH$_3$, —OC$_2$H$_5$, —O—C$_3$H$_7$ or —OC$_4$H$_9$.

* * * * *

UNITED STATES PATENT AND TRADEMARK OFFICE
CERTIFICATE OF CORRECTION

PATENT NO. : 6,998,129 B2
APPLICATION NO. : 10/179955
DATED : February 14, 2006
INVENTOR(S) : Lionel Breton et al.

It is certified that error appears in the above-identified patent and that said Letters Patent is hereby corrected as shown below:

Column 2, lines 42, "Ingre-" should read --ingre- --;

43, "Inflammatory" should read --inflammatory--;

54, "Including" should read --including--.

Column 5, line 59, "$R_6$" should read --$R_5$--.

Column 6, line 4, "Are also included In such definition, the mineral or" should read --Also included in such definition are the mineral or--;

Column 7, lines 7, "3-máthyl-" should read --3-méthyl- --;

43, "Invention" should read --invention--;

67, "Are also included in the definition of an antago-" should read

--Also included in the definition of an antago---;

Column 8, lines 1, "nist of the inflammatory cytokines, the compounds inhibit-;" should read --nist of the inflammatory cytokines are the compounds inhibit--.

6, "Are included amongst the antagonists of the inflammatory" should read --Included amongst the antagonists of the inflammatory--;

7, "Lys-Pro-Vat" should read -- Lys-Pro-Val--;

31, "Invention" should read --invention--.

Column 9, line 41, "Are included amongst the fatty phase components" should read --Included amongst the fatty phase components are:--;

59, "triglyceride" should read --triglycerides--.

UNITED STATES PATENT AND TRADEMARK OFFICE
CERTIFICATE OF CORRECTION

| | |
|---|---|
| PATENT NO. | : 6,998,129 B2 |
| APPLICATION NO. | : 10/179955 |
| DATED | : February 14, 2006 |
| INVENTOR(S) | : Lionel Breton et al. |

It is certified that error appears in the above-identified patent and that said Letters Patent is hereby corrected as shown below:

Column 15, line 63, "LPV tripeptide" should read -- KPV tripeptide--.

Column 16, line 32, "LPV tripeptide" should read -- KPV tripeptide--.

Signed and Sealed this

Sixteenth Day of January, 2007

JON W. DUDAS
*Director of the United States Patent and Trademark Office*